(12) United States Patent
Horst et al.

(10) Patent No.: US 9,323,897 B2
(45) Date of Patent: Apr. 26, 2016

(54) MEDICATION DISPENSER

(75) Inventors: Meriete Horst, Eindhoven (NL);
Georgio Mosis, Eindhoven (NL);
Ronald Leo Christiaan Koymans,
Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 395 days.

(21) Appl. No.: 13/500,143

(22) PCT Filed: Sep. 30, 2010

(86) PCT No.: PCT/IB2010/054416
§ 371 (c)(1),
(2), (4) Date: Apr. 4, 2012

(87) PCT Pub. No.: WO2011/042840
PCT Pub. Date: Apr. 14, 2011

(65) Prior Publication Data
US 2012/0199650 A1    Aug. 9, 2012

(30) Foreign Application Priority Data

Oct. 5, 2009  (EP) .................................... 09172170

(51) Int. Cl.
*G06F 17/00* (2006.01)
*G06F 19/00* (2011.01)
(Continued)

(52) U.S. Cl.
CPC ............ *G06F 19/3462* (2013.01); *G07F 11/68* (2013.01); *G07F 17/0092* (2013.01); *A61J 2200/30* (2013.01)

(58) Field of Classification Search
USPC ........................................................ 235/375
See application file for complete search history.

(56) References Cited

U.S. PATENT DOCUMENTS

| 4,971,221 A | 11/1990 | Urquhart et al. |
| 5,657,236 A | 8/1997 | Conkright |
| 5,945,651 A * | 8/1999 | Chorosinski ......... G06Q 10/087 235/375 |

(Continued)

FOREIGN PATENT DOCUMENTS

| WO | 2005022323 A2 | 3/2005 |
| WO | 2006050295 A1 | 5/2006 |

OTHER PUBLICATIONS

Kannry, Joseph et al "MediSign: Using a Web-Based SignOut System to Improve Provider Identification" Center for Medical Informatics, Mount Sinai Medical Center, NY, NY, 1999, AMIA, Inc, pp. 550-554.

(Continued)

*Primary Examiner* — Michael G Lee
*Assistant Examiner* — David Tardif

(57) ABSTRACT

A medication dispenser comprises a body with an opening, an advancing device, a reader, an output device and a processor connected to the advancing device, the reader and the output device. The body is closable and lockable and is arranged to receive a medication container comprising multiple individual sealed medication chambers, each medication chamber including a data tag relating to the medication chamber. The opening in the body is for a medication chamber and the advancing device is arranged to advance a medication chamber through the opening. The reader is arranged to read a data tag on a medication chamber and the processor is arranged to control the advancing device and the output device, according to a data tag on a medication chamber.

14 Claims, 6 Drawing Sheets

(51) Int. Cl.
*G07F 11/68* (2006.01)
*G07F 17/00* (2006.01)

(56) References Cited

U.S. PATENT DOCUMENTS

| | | |
|---|---|---|
| 2003/0023146 A1* | 1/2003 | Shusterman, D.O. ............... A61B 5/02055 600/300 |
| 2004/0094564 A1 | 5/2004 | Papp |
| 2004/0133305 A1 | 7/2004 | Jean-Pierre |
| 2005/0049747 A1 | 3/2005 | Willoughby |
| 2008/0059228 A1* | 3/2008 | Bossi ............... G06F 19/3418 705/2 |
| 2008/0114490 A1 | 5/2008 | Jean-Pierre |
| 2009/0001093 A1 | 1/2009 | Labhard |

OTHER PUBLICATIONS

Medisign, Web Applications Integrated Intranet & Internet Solutions, May 205, Ver.3, pp. 1-12.

\* cited by examiner

MEDICATION DISPENSER

TECHNICAL FIELD OF THE INVENTION

This invention relates to a medication dispenser. The dispenser, in one embodiment, provides apparatus to monitor and support medication management in a home environment and on the move.

BACKGROUND TO THE INVENTION

There are an increasing number of people who are taking multiple medications each day. Studies have shown that about half of these people do not take their medication correctly. Taking medication incorrectly can result in medication related problems that can be fatal, can lead to hospital and nursing home admissions and contribute to prolonged or additional illnesses in the patient. According to research, many elderly patients using pillboxes do not follow recommended practices. In the USA, medication related problems are estimated to amount to a total cost of approximately $600-$800 million per year. With an increasing group of senior citizens, this number is expected to rise.

Currently, different devices are available to help patients organize medication, to remind patients to take their medication or to monitor the patient's adherence. Once such medication organization device that can be used by a patient is the Simpill, see http://www.simpill.com/ for further information. The Simpilll is comparable to a normal seven day, four times a day, pill box, with the added feature of monitoring the user's behavior. This pill box sends a timestamp to a central server when the lid has been opened and closed. However, the user has to fill the pill box. Simpill also has a reminder function, but it will only remind the user when the medication has not been taken in time, for example the device will then send an SMS to remind the user to take their medication. If the user still does not take their medication, a caregiver can be notified via SMS. A pharmacist has access to a secured web site with the information about the compliance of the patient. Each month the user receives a report with a summary of the achieved results.

A second device is Dispense-a-pill by HealthOneMed, see http://www.dispenseapill.net/dap.html. This device will dispense the right amount of medication from a container with one type of medication. The device can hold up to eight different containers. When there is a change in the medication schedule, the user can adapt this via the interface of the device. When the medication is not in a pill form, a reminder can also be programmed into the device, for example a reminder to take an insulin injection. The dispenser is not readily portable, and therefore does not offer anything in which the user can take along their medications, for taking an early dose, for example.

A further device is EMMA® by INRange Systems Inc, see http://www.inrangesystems.com/, for further information. This device is programmed by the patient's health-care provider and can dispense individual doses of ten different drugs for up to a month's supply. Prescriptions and refills are prepared in blister cards dispensed by a pharmacy to the patient; the cards are then loaded into the dispenser. They have a barcode, so the dispenser knows which medication has been inserted. Use is supervised by the patient's healthcare team which, through a web-based, remote connection, can modify dosages and schedules of contained drugs. These licensed professionals can make real-time dose and timing changes.

Another device is MedReady, see http://www.medready-.inc.com/. Medready is a unit that is lockable, preventing a person from inadvertently overdosing. The unit has twenty-eight compartments to hold medication and can be programmed to deliver up to four doses a day. The unit rotates and, at the pre-set times, the alarm rings and a door can be opened to access the appropriate medication. By opening the door to access the medication, the alarm is silenced. With proper use, a person should be able to adhere to the medication schedule. The user is responsible for sorting out the medication scheme. MedReady can hold twenty-eight dosages, and has up to four alarms a day. For many patients, particularly those on complex medication schedules who may need up to eight doses a day, this device cannot provide sufficient medication over a long-enough period of time.

A final prior art device is Philips MD2, also referred to as Personal Medication Dispenser, see for example http://www.epill.com/md2.html. Using a programmed schedule, the MD2 device dispenses cups with a dose of medication that have been put into the device. The MD2 can hold up to sixty dosages, and has up to six alarms a day. In practice, people often write date and time on the cups to be sure which dosage it is. When programmed, the programming buttons are hidden for the end user, and only one button remains, the one that stops the alarm and dispenses the cup with medications.

All of the current pill dispensers, except the EMMA system, rely on the user to sort out the medication scheme and to program the device. This point is regarded as difficult by users and considered to be error prone. Consequently this task is often done by caregivers reducing the autonomy and independence of the people taking the medication. Furthermore, none of the current medication management devices offer a reminder that is 'on-body', so it is expected that the user will be in range of the product, at least at the times they will need to take their medication. Also, conventional pill dispensers and medication management systems do not give enough feedback to the patients and the caregivers to prevent errors. As a consequence patients continue to be non-compliant to their medication regimen. It is therefore an object of the invention to improve upon the known art.

SUMMARY OF THE INVENTION

According to a first aspect of the present invention, there is provided a medication dispenser comprising a closable and lockable body arranged to receive a medication container comprising multiple individual sealed medication chambers, each medication chamber including a data tag relating to the medication chamber, the body including an opening for a medication chamber, an advancing device arranged to advance a medication chamber through the opening, a reader arranged to read a data tag on a medication chamber, an output device arranged to generate an output, and a processor connected to the advancing device, the reader and the output device and arranged to control the advancing device and the output device, according to a data tag on a medication chamber.

According to a second aspect of the present invention, there is provided a method of operating a medication dispenser, the dispenser comprising a closable and lockable body, the body including an opening for a medication chamber, an advancing device, a reader, an output device and a processor connected to the advancing device, the reader and the output device, the method comprising the steps of receiving, in the dispenser body, a medication container comprising multiple individual sealed medication chambers, each medication chamber including a data tag relating to the medication chamber, advancing a medication chamber through the opening, reading a data tag on a medication chamber, generating an output, and controlling the advancing and the outputting, according to a data tag on a medication chamber.

Owing to the invention, it is possible to provide a medication management system that uses methods that are effective combined with innovations to give the users and the caregiver the proper feedback. The medication management system reminds the patient, gives the patient situational feedback and also provides the patient with a medication management solution even if the patient is on the move. The system can also provide a feed forward medication delivery, for example by providing and instructing the patient in relation to an early dose, which may be required if the patient is likely to be travelling for example. The invention also addresses the issue of medication non-adherence. It is a solution which comprises a pill dispenser, which allows caregivers to monitor the patient's adherence. As such the safety and effectiveness of the therapy is achieved.

Preferably, the dispenser further comprises a detector connected to the processor and arranged to detect that an advanced medication chamber has been removed. The dispenser can be provided with means for detecting that a medication chamber, which has been ejected via the opening, has actually been removed by the patient. This provides a way of assisting in monitoring the patient's observance of the medication program, as the dispenser can determine when a medication chamber has not been used and can also be aware that a patient has removed the relevant medication chamber from the medication container. To further assist in the monitoring, the processor can be arranged to record the time at which the advancing device advances a medication chamber through the opening.

Advantageously, the dispenser further comprises a color system connected to the processor, wherein the processor is arranged to control the color system according to a data tag on a medication chamber. The color system can be used to provide feedback to the user in a simple fashion. Different colors can be used to indicate different things to the patient. For example, when it is time for a patient to take their medication, and a medication chamber is going to be dispensed from the dispenser, then a specific known color can be used as an alert to the patient from the color system. Other colors can be used to indicate situations such as overdue medication, and so on.

Ideally, the dispenser further comprises a motion detector connected to the processor, wherein the motion detector is arranged to detect the presence of a user and accordingly to trigger reading of a data tag on a medication chamber. The motion detection device can be a touch based device which only operates when directly touched by the patient, or can operate by the detection of movement within a certain range of the device. The motion detection device can be used to determine that a patient is present and that the advancing device can dispense a medication chamber to that patient. The motion detection system can also be used in conjunction with other user interface components of the dispenser, such as the output device and the color system to provide feedback to the user, for example, in response to the user seeking medication from the dispenser, when it is not actually time for a medication chamber to be dispensed.

Advantageously, the dispenser further comprises a network connector connected to the processor and to an external server, wherein the processor is arranged to communicate with the external server. Preferably, a data tag relating to the medication chamber comprises either data relating to the medication stored in the medication chamber or a link to such data, stored on a database at the server. By connecting to a remote server, various additional functionality of the dispenser is possible. The vastly improves the ability of the dispenser to assist in the delivery of the medication program to the patient. Remote monitoring of the dispenser and of the medication dispensing is possible, which will go towards ensuring that any problems with either the dispenser or the medication program are picked up as early as possible.

Preferably, the processor is arranged to communicate a read data tag to the external server, to receive a confirmation message from the server in response, and to operate the advancing device to advance a medication chamber through the opening, only after receipt of the confirmation message. The connection to the remote server can also be used to check each medication chamber that is about to be dispensed. When a data tag on a specific medication chamber is read and the processor, via a timing mechanism, is about to dispense that medication chamber, the processor can communicate that data tag to the remote server. A checking function can then be carried out at the server, and the medication chamber will only be dispensed by the dispenser, if the correct confirmation message is returned by the server.

Ideally, the processor is arranged to communicate a read data tag to the external server, to receive an output message from the server in response, and to operate the output device according to the output message. Alternatively, or additionally to the confirmation message, an output message can also be sent back by the remote server to the dispenser. Again, when a data tag is read and the processor is about to dispense the associated medication chamber, the processor can communicate that data tag to the remote server and receive back an output message which will be output by the dispenser. This message can be about the specific medication being dispensed, for example, how the patient should consume the medication "take with water", for example. The message may be more general, "avoid alcohol for 3 hours" or may relate to the patient directly "doctor's appointment 3 pm". This also makes it possible for the user to properly react to changing medication schemes. This use of a messaging system with the dispenser provides great flexibility in the delivery of a healthcare program to a patient. Remotely, the patient's data can be monitored and interpreted, either automatically and/or by a suitably qualified physician. This can be used to provide messages that are applicable directly for that patient and for the medication that they are taking via the dispenser.

BRIEF DESCRIPTION OF THE DRAWINGS

Embodiments of the present invention will now be described, by way of example only, with reference to the accompanying drawings, in which:—

DETAILED DESCRIPTION OF THE PREFERRED EMBODIMENTS

Figure 1:
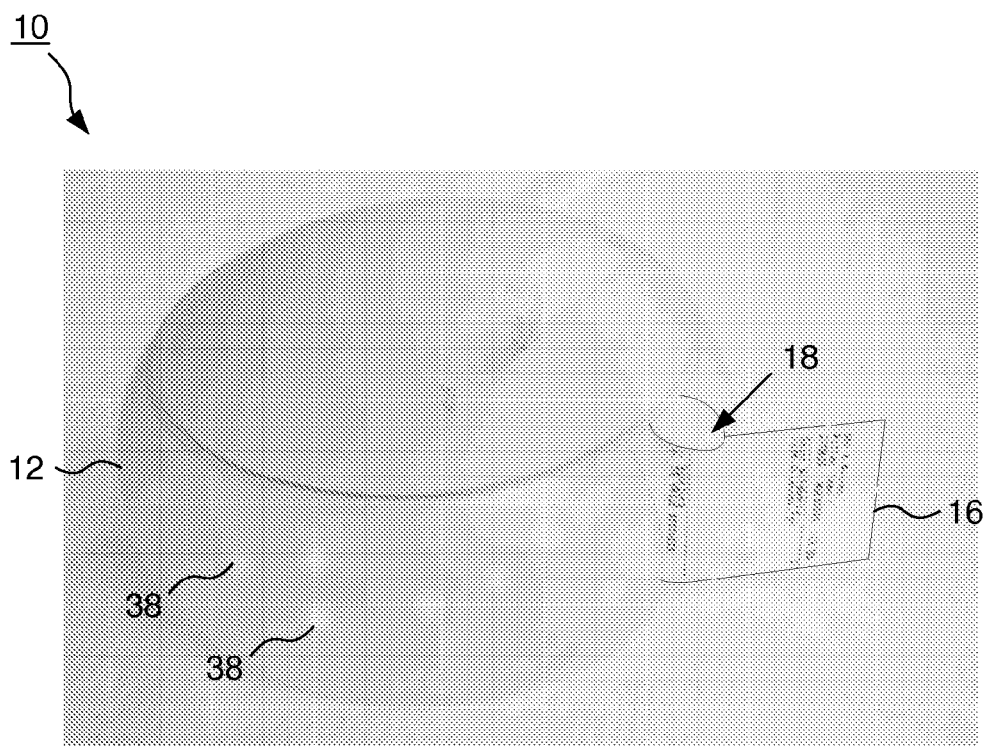
FIG. 1 is a schematic diagram of a medication dispenser.
Figure 2:
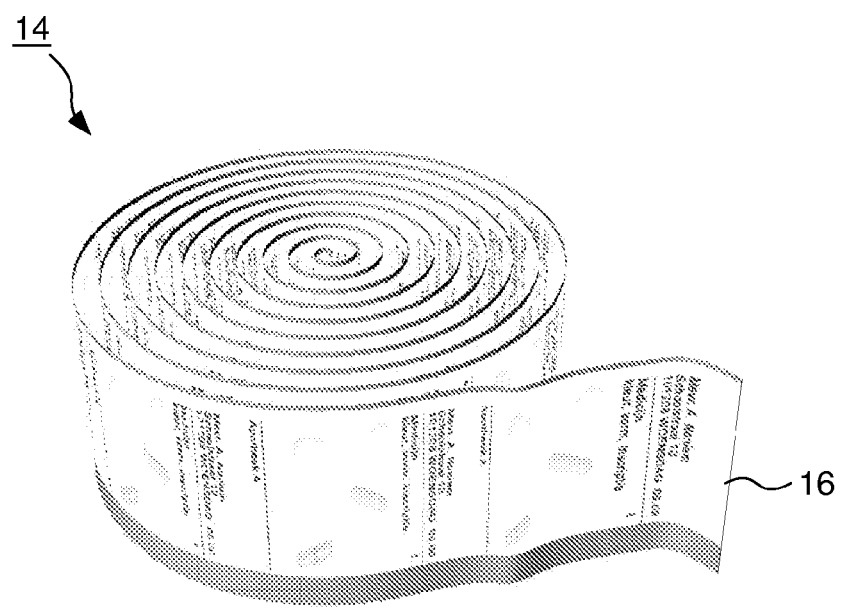
FIG. 2 is a schematic diagram of a medication container.

FIGS. 1 and 2 show a medication dispenser 10 which comprises a closable and lockable body 12. The body 12 is arranged to receive a medication container 14. The medication container 14 is a flexible roll of transparent plastics material and comprises multiple individual sealed medication chambers 16, each medication chamber 16 including a data tag (in this case a barcode) relating to the medication chamber 16. The data tag either contains information about the medication within the specific medication chamber 16 or will contain a link (such as a URL) to a data source that contains this information. The body 12 also includes an opening 18 for a medication chamber 16 to be expelled from the dispenser 10. The body 12 also includes colored LEDs 38 for changing the color of the dispenser 10. The operation of these LEDs 38 is described in more detail below.

The medication management system consists of the medication container 14 (which in this case is a Baxter roll 14), the pill dispenser 10, and also a remote server and a database as described in more detail below. The Baxter roll 14 consists of individual bags 16 each containing a dose that the patient needs to take at a specific point of time. The Baxter roll 14 contains the patient information (such as name and address) and the metadata about the medication that is in the package 16 (such as medication moment, medication contents, medication description and pharmacist's name). For decision support purposes, a barcode (the data tag) is added to the current Baxter roll 14 on each individual bag 16 with a medication dose, and on the roll 14 as a whole which contains data of all different medications the roll 14 contains.

FIG. 2 shows the Baxter roll 14 with medication metadata and with additional barcode that will be used for decision support purposes. The roll 14 is placed inside the intelligent design pill dispenser 10, as depicted in FIG. 1. The dispenser 10 holds the Baxter roll 14 and has the ability to monitor the compliance of the patient taking medication via the Baxter roll 14. More details on the functionality of the pill dispenser 10 are provided in the discussions below on patient feedback mechanism and interaction with the user. The dispenser 10 is preferably connected to a remote server containing the monitoring information of the device 10, this is discussed in more detail below with reference to FIG. 5. The server also contains the medication schemes and an electronic medication record of the device user. The barcodes on the Baxter roll 14 are linked to a database containing metadata about the medication in the roll 14. The metadata consists of a structured coding system to identify the medication in the roll 14, tailored information about the medication such as how to take the medication and dosing advice. The metadata is from a trusted source backed by a professional organization maintaining the information, for example Pharmaco-Therapeutic-Guides (see http://www.fk.cvz.nl, for example for more information.

Figure 3:
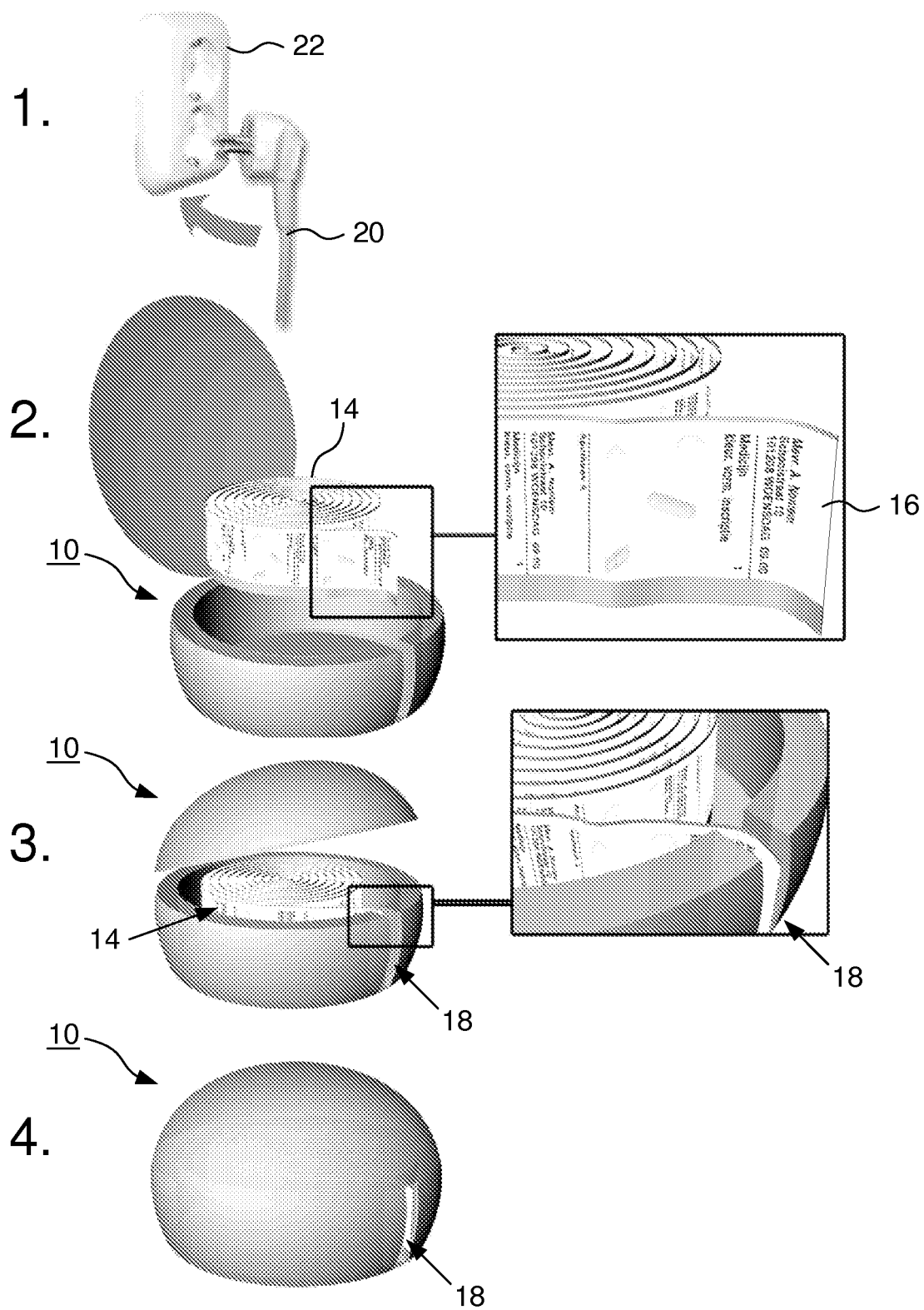
FIG. 3 is a schematic diagram of a method of using the medication dispenser.

The Baxter roll 14 with the additional barcode in the dispenser 10 enables one or more professionals to monitor the medication compliance of the patient to the medication regime. FIG. 3 shows how a user can operate the dispenser 10. Firstly, the user connects the dispenser 10 with a power cable and plug 20 to a socket 22 and then, secondly, the Baxter roll 14 is placed in the dispenser 10. The dispenser 10 is primarily powered by a traditional power supply from the wall socket 22, but is also equipped with a local battery. This enables users to take the dispenser 10 with them when they are on the move. At stage three, the medication container 14 (the Baxter roll 14) is placed inside the dispenser 10 in such a way that the opening 18 has the end of the roll 14 threaded through. The Baxter roll 14 is in the dispenser 10 to enable monitoring of compliance to the medication regimen. At stage four, the dispenser 10 is closed and locked, ensuring that the medication container 14 can no longer be accessed except through the opening 18. Any dispensing of the individual medication chambers 16, which make up the roll 14, is through the opening 18. In this way, a patient will receive the individual chambers 18 from the roll 14, which has been prepared by a licensed pharmacist.

Figure 4:
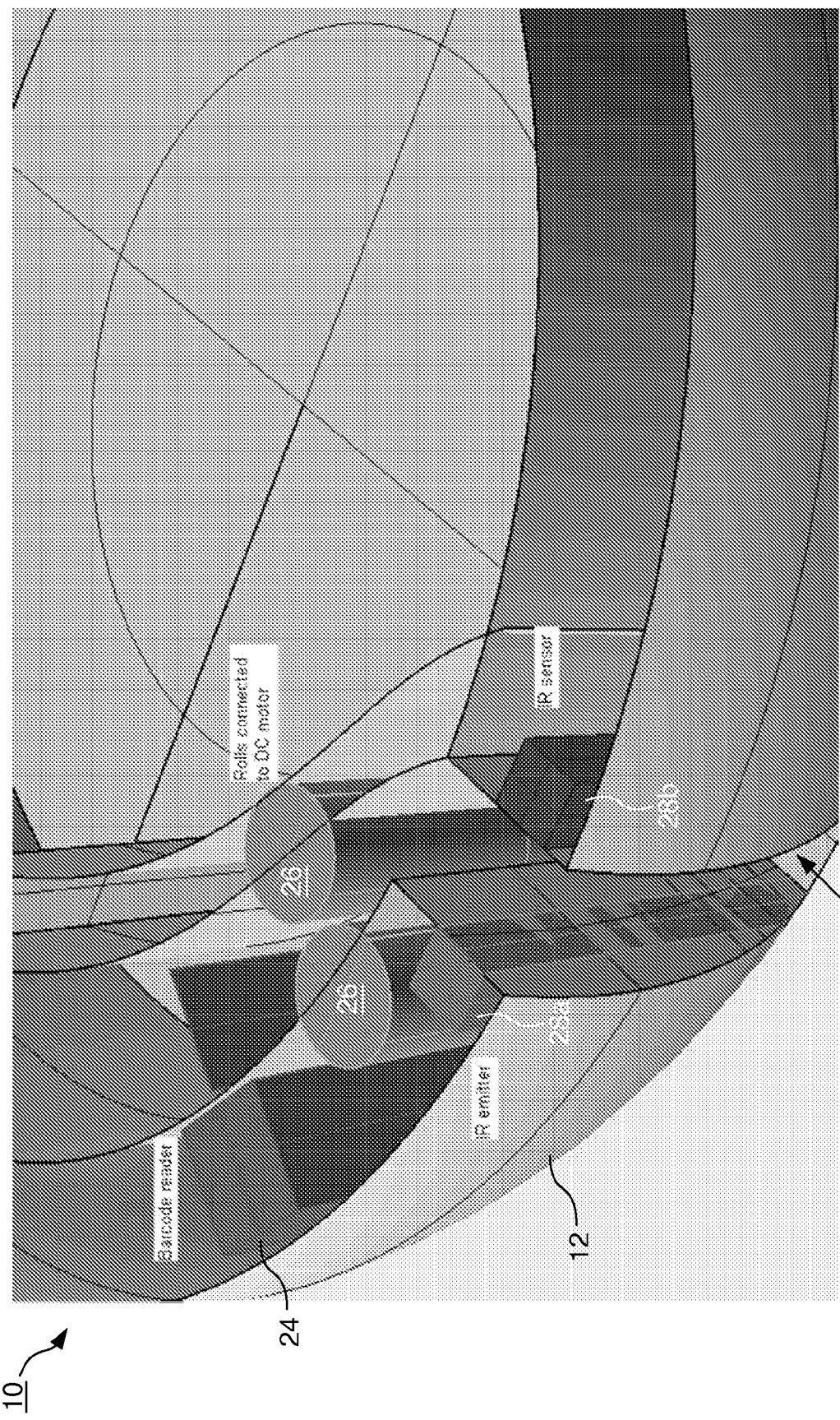
FIG. 4 is a schematic diagram of internal components of the medication dispenser.

The dispenser 10 is equipped with a special mechanism, as shown in FIG. 4, to read the barcode on the Baxter roll 14. The dispenser 10 is also equipped with a suitable internal cutting device (not shown) to tear off a bag 16 from the Baxter roll 14 containing just the dose of one moment of medication intake. The bag 16 is removed from the roll 14 by the cutting device. The dispenser 10 dispensing part contains the following elements: a barcode reader 24 to read the barcode with medication information from the Baxter roll 14, a detector 28 formed of an infrared emitter 28a and an infrared sensor 28b to monitor the proper ripping of the Baxter roll 14 into chambers 16 and mechanical rolls 26 which are supported by DC motors and transport the Baxter roll 14 forwards, advancing the individual chambers 16 of the roll 14 through the opening 18 of the medication dispenser 10.

FIG. 4 shows a detailed view of the mechanism to read the barcode on the Baxter roll 14 and to rip the Baxter roll 14 into the packages 16 of medication in time-dependent dosing units. There are two options to get the Baxter roll 14 into the dispenser 10. Firstly, the dispenser 10 can be opened up and the Baxter roll is then placed into the body of the device as indicated in FIG. 3. The second option is to use the output interface 18 to enter the roll 14 in reverse. The DC motors operating the mechanical rolls 26 will reverse their direction to "swallow" the roll 14 in an opposite direction. Thereafter, the dispenser 10 is ready to dispense the packages 16 in the right order to the patient.

The mechanical rolls 26, which are each powered by a DC motor, make up an advancing device 26 which is arranged to advance the medication chambers 16 of the Baxter roll 14 through the opening 18 of the dispenser 10. The reader 24 is arranged to read a data tag on a medication chamber 16. When it is time for a medication chamber 16 to be expelled from the dispenser 10, then the barcode reader 24 will read the data tag on the current chamber 16 and the advancing device 26 will advance the Baxter roll 14, such that a single medication chamber 16 is advanced through the opening 18. The cutting device will then cut off this chamber 16 from the roll 14. The user can then remove the chamber 16 and this action is verified by the detecting system 28.

Figure 5:
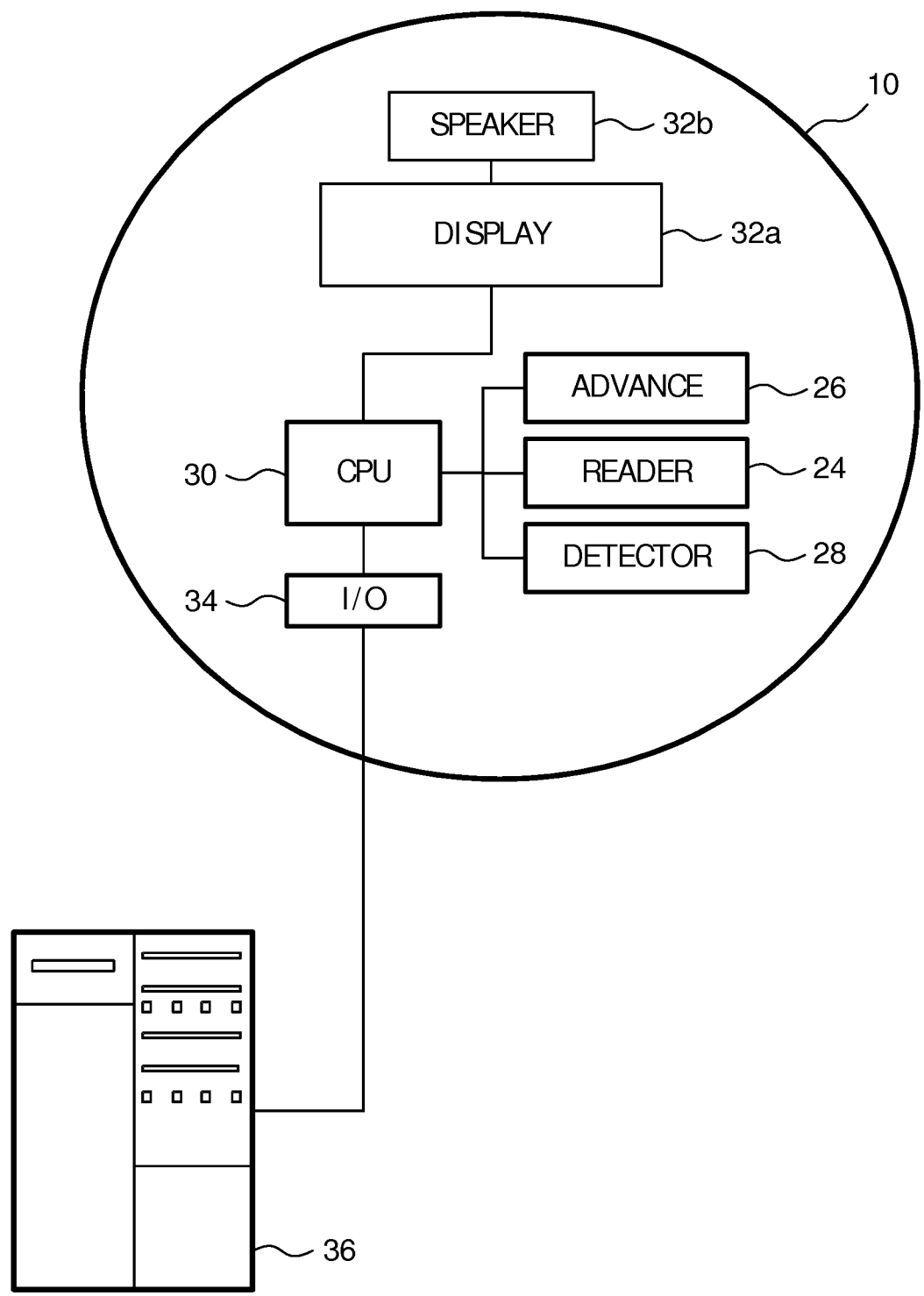
FIG. 5 is a schematic diagram of the medication dispenser connected to a server.

The dispenser 10 also includes a processor 30 and an output device 32, as shown in FIG. 5. The output device 32 is arranged to generate an output, and in this embodiment, the output device 32 comprises a display device 32a and an audio output device 32b. The processor 30 is connected to the advancing device 26, the reader 24, the detector 28 and the output device 32 and is arranged to control the advancing device 26 and the output device 32, according to a data tag on a medication chamber 16. The overall control of the dispenser 10 is under the operation of the processor 30. The dispenser 10 also comprises a network connector 34 connected to the processor 30 and to an external server 36, where the processor 30 is arranged to communicate with the server 36, through the network connector 34.

The dispenser 10 is operated in such a way so as to provide a patient feedback mechanism. When the barcode reader 24 captures the information from the Baxter roll 14 about a specific medication chamber that is about to be dispensed, this information is compared with metadata that is stored on the server 36. Firstly, a safety check is carried out to see if the right medication is being dispensed to the right person at the right time. Once this check is verified, the dispenser 10 rips the roll 14 into a dosing unit 16 for that specific time. The server 36 then sends back information that is specific to the user for that moment in time. This patient education material is an information package which can consist of sound, texts, icons and colors, according to the functionality delivered by the output device 32. This package is then processed by the dispenser 10 (specifically the processor 30) according to the context. For example, the output device 32 may display an icon indicating the use of the medication, if audio output means are present, a sound to specifically educate the patient on how to take the medication and text for those who have hearing impairment. The use of colors, mentioned above, is described in more detail below.

Figure 6:
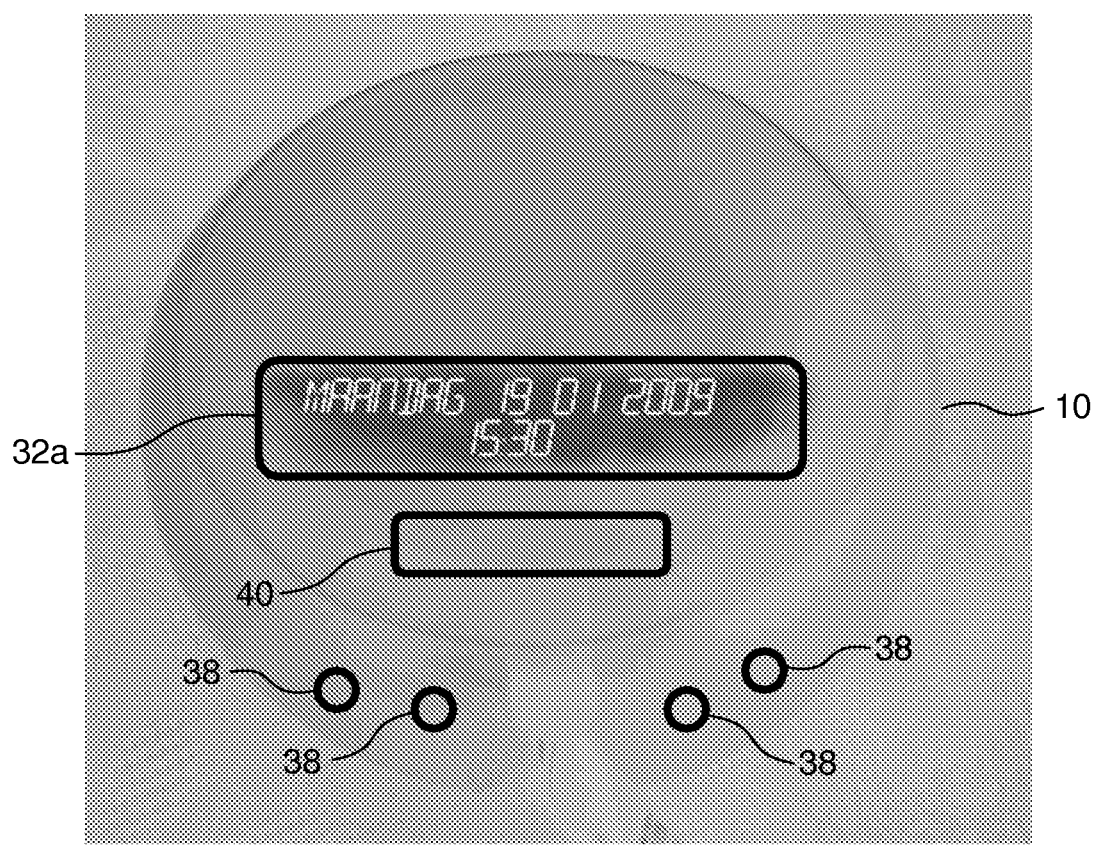
FIG. 6 is a further schematic diagram of the medication dispenser.

In a preferred embodiment, the dispenser's user interface provides the ability to communicate medication specific information in text, sound and in color to the patient. The dispenser 10 can also be configured to provide situational visual alerts. To achieve this, the dispenser 10 is able to change color. This can be achieved by the use of the different color LEDs, which form a color system 38 within the body 12 of the dispenser 10, as shown in FIG. 1 and FIG. 6. In addition to the display 32a, the dispenser 10 is provided with the color system 38. The colors that are outputted by the color system 38 are indicative of a desired or undesired situation that is known and understood by the patient. The system 38 changes color when there is an error or when specific attention is required from the patient.

The dispenser color indicator 38 is used to communicate information to the user during interaction with the user. For example, the dispenser 10 may include a motion detection device 40, as is shown in the embodiment of FIG. 6. The motion detection device 40 can detect movement within a short range of about 5 cm. When the patient puts a hand above the motion detection device 40, the dispenser 10 will dispense the medication. However, this only happens when it is time for the patient to take the medication. In order to enable this procedure, the dispenser 10 is equipped with the touch sensors 40 on top of the dispenser 10.

In relation to the dispensing of the medication, four scenarios are distinguished by the dispenser 10. The first scenario is medication dispensed on time. When it is time for the user to take their medication, the dispenser 10 will light up and subsequently play a sound. The user should than put their hand above the motion detection device 40. This is registered by the sensor 40 and as a result the next barcode on the Baxter roll 14 is read, the Baxter roll 14 is ripped off and the resulting Baxter package 16 will be dispensed. The dispenser 10 uses icons, text messages and sounds to instruct the user about how to take the medication and when the next dosing moment will be ready.

The second scenario relates to the situation in which the user is too early for medication. When it is not time for the patient to take their medication and the user puts their hand above the motion sensitive device 40, the dispenser 10 will change color, indicating that it is not time to take the medication. Text and sound will accompany the changing color to support the user's understanding of the situation. However, the third scenario relates to an early dose. When a patient requires an early dose, for example before they travel a long distance, they can hold their hand above the device 40 for a fixed period of time (a few seconds, for example). The feedback lights 38 will change and the user will be asked if they want an early dose. Instructions on how to get the proper amount of doses will also be given. On a positive feedback, the dispenser 10 will carry out the scenario of the medication on time (one dose at a time). The final scenario is that of the user being too late. When a patient misses a dose, the dispenser 10 will change color, indicating that a dose was missed. Text messages and sound will inform the user on what to do to catch up with the treatment regime.

Figure 7:
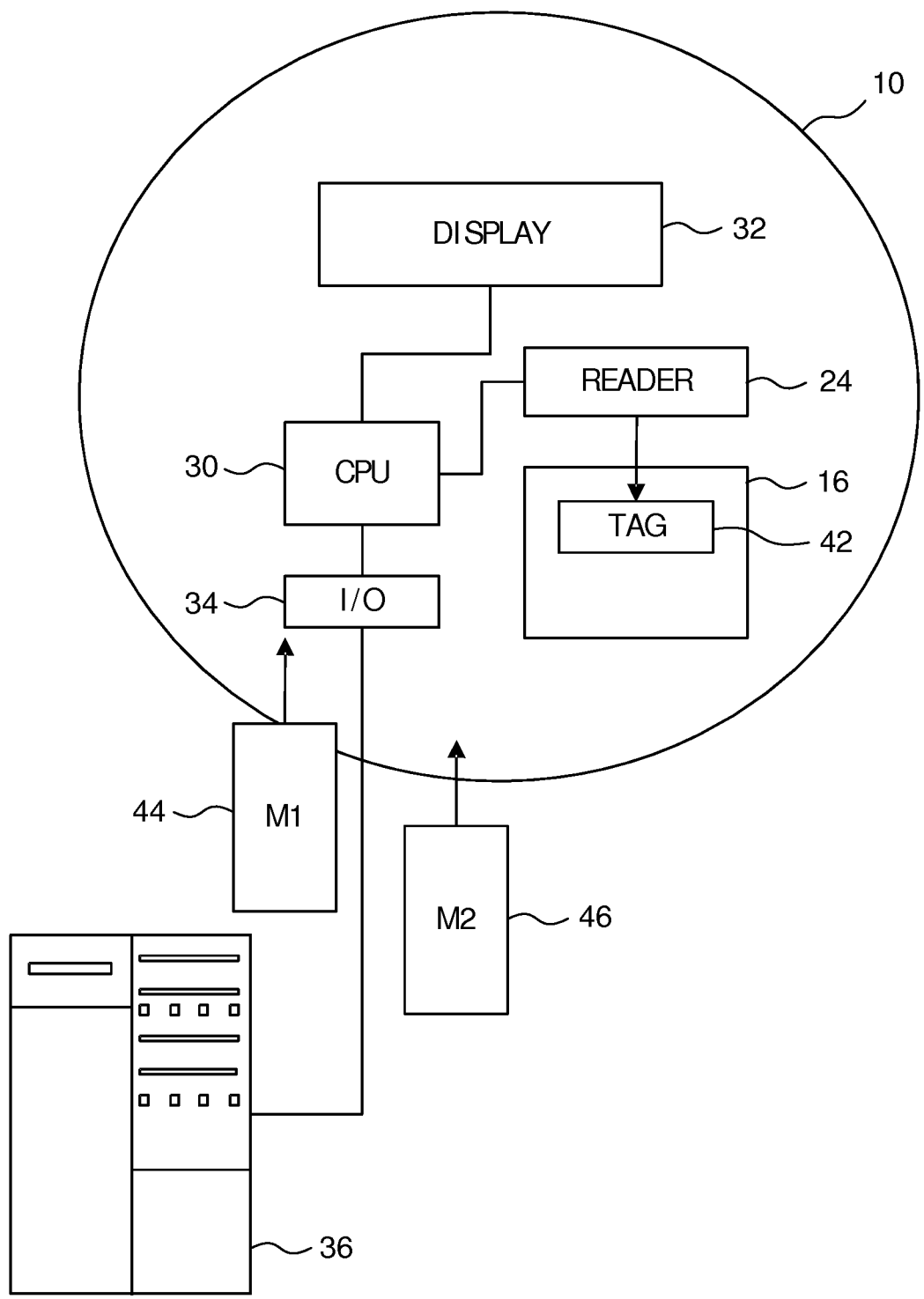
FIG. 7 is a further schematic diagram of the medication dispenser connected to the server, showing data traffic.

The communication of messages by the server 36 back to the dispenser 10 is illustrated in FIG. 7. The reader 24 is arranged to read a data tag 42 on a medication chamber 16. This chamber 16 is the next chamber 16 that is to be dispensed to the patient. The processor 30 is arranged to communicate the read data tag 42 to the external server 36, and receives a confirmation message 44 from the server 36 in response. The processor 30 operates the advancing device 26 (not shown in this Figure for clarity purposes) to advance the medication chamber 16 through the opening 18, only after receipt of the confirmation message 44.

Similarly, the processor 30 is arranged to communicate the read data tag 42 to the external server 36, and to receive an output message 46 from the server 36 in response, and operates the output device 32 according to the output message 46. This message 46 can be about the specific medication in the chamber 16, for example, how the patient should consume the medication. The message may be more general or may relate to the patient directly. The delivery of messages to the dispenser 10 from the server 36 allows data received from the dispenser 10 to be monitored and interpreted, in order to provide messages that are applicable directly for the patient and for the medication that they are receiving from the dispenser 10.

The applications of the dispenser 10 are to provide a medication management solution, which is applicable to elderly using multiple medications and who are not able to manage their medication themselves. Since Baxtering of medication is widely used in the European Union (and indeed in some of the European countries, it is already arranged by law to pre-pack the patient's medication in a Baxter roll) the dispenser 10 is ideally suited to the delivery of medication programs to patients in such a manner that will alleviate the load on the patient, as the medication is pre-packed and dispensed directly to them. The dispenser 10 is provided with output means that can be used to inform the patient about the medication they are taking. The network link can be used to monitor the dispenser 10 and the delivery of medication to the patient and can also provide a back-channel by which patient specific information can be generated and provided directly to the patient when they are about to take their medication.

The invention claimed is:

1. A medication dispenser comprising:
   a closable and lockable body arranged to receive a medication container comprising multiple individual sealed medication chambers, each medication chamber including a data tag conveying information related to medication in that chamber, the body including an opening for dispensing the medication chambers,
   an advancing device arranged to advance the medication chambers through the opening,
   a reader arranged to read the data tag on each medication chamber,
   an output device arranged to generate an output,
   a color system within the body configured to change a color of the body at a time when an individual medication chamber should be advanced through the opening,
   a motion detector coupled with the body configured to detect motion by a user in proximity to the body,
   a processor connected to the advancing device, the reader, the output device, the color system, and the motion detector, and arranged to control the advancing device, the output device, and the color system according to the information conveyed by the data tag on each medication chamber and information conveyed by the motion detector, and a network connector electronically coupled with the processor, wherein the processor is arranged to communicate with an external server via the network connector, and wherein the processor:
- causes the color system to change the color of the body at the time when the individual medication chamber should be advanced through the opening;
- receives an indication from the motion detector of motion by the user responsive to the change in color of the body;
- communicates the information stored on a data tag for the individual medication chamber to the external server and receives a confirmation message from the external server that indicates the medication in the individual medication chamber should be delivered; and
- controls the advancing device to dispense the individual medication chamber responsive to receiving the confirmation message.

2. A dispenser according to claim 1, and further comprising a detector connected to the processor and arranged to detect that an advanced medication chamber has been removed.

3. A dispenser according to claim 1, wherein the processor is arranged to record the time at which the advancing device advances a medication chamber through the opening.

4. A dispenser according to claim 1, wherein the information relating to the medication in the chambers comprises either data relating to the medication stored in each medication chamber or a link to such data.

5. A dispenser according to claim 1, wherein the color system is further configured to, responsive to the motion detector detecting the motion of the user not at a time when the individual medication chamber should be advanced through the opening, change the color of the body to a different color than the color used at the time when the individual medication chamber should be advanced through the opening.

6. A dispenser according to claim 1, wherein the motion detector is arranged to detect motion of a user's hand within about 5 cm of the body.

7. A dispenser according to claim 1, wherein the confirmation message received by the processor indicates successful completion of a safety check by the external server indicating that it is safe for the medication in the individual medication chamber to be delivered.

8. A dispenser according to claim 1, wherein the confirmation message received by the processor includes audio and/or visual patient education material associated with the medication in the individual medication chamber, and wherein the processor causes the audio and/or visual patient education material to be delivered by the output, such audio and/or visual information including instructions that indicate how the medication in the individual medication chamber should be taken.

9. A method of operating a medication dispenser, the dispenser comprising a closable and lockable body, the body including an opening for dispensing medication chambers, an advancing device, a reader, an output device, a color system, a motion detector, a network connector, and a processor coupled with the advancing device, the reader, the network connector, the output device, the color system, and the motion detector, the method comprising:
- receiving, with the dispenser body, a medication container comprising multiple individual sealed medication chambers, each medication chamber including a data tag conveying information related to medication in each chamber,
- changing a color of the body at a time when an individual medication chamber should be advanced through the opening,
- detecting motion by a user in proximity to the body,
- advancing medication chambers through the opening,
- reading the data tag on each medication chamber,
- generating an output, and
- controlling the color changing, the advancing, and the outputting according to the information conveyed by the data tag on each medication chamber and the detected motion by the user, wherein controlling includes:
  - causing the color system to change the color of the body at the time when the individual medication chamber should be advanced through the opening;
  - receiving an indication from the motion detector of motion by the user responsive to the change in color of the body; and
  - communicating, via the network connector, information stored on a data tag for the individual medication chamber to an external server, and receiving a confirmation message from the external server that indicates the medication in the individual medication chamber should be delivered; and
  - controlling the advancing device to dispense the individual medication chamber responsive to receiving the confirmation message.

10. A method according to claim 9, and further comprising detecting that an advanced medication chamber has been removed.

11. A method according to claim 9, and further comprising recording the time at which the advancing device advances a medication chamber through the opening.

12. A method according to claim 9, and further comprising detecting motion of a user's hand within about 5 cm of the body.

13. A method according to claim 9, wherein the confirmation message from the external server received by the processor indicates successful completion of a safety check by the external server indicating that it is safe for the medication in the individual medication chamber to be delivered.

14. A method according to claim 9, wherein the confirmation message from the external server received by the processor includes audio and/or visual patient education material associated with the medication in the individual medication chamber, and wherein the audio and/or visual patient education material is delivered by the output, such audio and/or visual information including instructions that indicate how the medication should be taken.

* * * * *